(12) United States Patent
Zhu et al.

(10) Patent No.: US 11,779,450 B2
(45) Date of Patent: Oct. 10, 2023

(54) FILTER DEVICE

(71) Applicant: SHANGHAI MICROPORT ENDOVASCULAR MEDTECH CO., LTD., Shanghai (CN)

(72) Inventors: Yongfeng Zhu, Shanghai (CN); Qing Zhu, Shanghai (CN); Zhonghua Li, Shanghai (CN); Linlin Zhang, Shanghai (CN); Wenhui Jiao, Shanghai (CN); Jianchao Han, Shanghai (CN); Yanbin Gao, Shanghai (CN)

(73) Assignee: SHANGHAI BLUEVASCULAR MEDTECH CO., LTD., Shanghai (CN)

( * ) Notice: Subject to any disclaimer, the term of this patent is extended or adjusted under 35 U.S.C. 154(b) by 8 days.

(21) Appl. No.: 16/627,592

(22) PCT Filed: Aug. 9, 2018

(86) PCT No.: PCT/CN2018/099490
§ 371 (c)(1),
(2) Date: Dec. 30, 2019

(87) PCT Pub. No.: WO2019/033977
PCT Pub. Date: Feb. 21, 2019

(65) Prior Publication Data
US 2020/0129281 A1 Apr. 30, 2020

(30) Foreign Application Priority Data
Aug. 18, 2017 (CN) .......................... 201710714197.9

(51) Int. Cl.
A61F 2/01 (2006.01)
A61F 2/04 (2013.01)

(52) U.S. Cl.
CPC .......... *A61F 2/0105* (2020.05); *A61F 2/0108* (2020.05); *A61F 2/04* (2013.01);
(Continued)

(58) Field of Classification Search
CPC .......... A61F 2/01; A61F 2/013; A61F 2/0103; A61F 2/0105; A61F 2/0108; A61F 2/012;
(Continued)

(56) References Cited

U.S. PATENT DOCUMENTS

2004/0059373 A1* 3/2004 Shapiro ..................... A61F 2/01
606/200
2008/0027481 A1* 1/2008 Gilson ....................... A61F 2/01
606/200
(Continued)

FOREIGN PATENT DOCUMENTS

CN 102824229 A 12/2012
CN 104434339 A 3/2015
(Continued)

Primary Examiner — Darwin P Erezo
Assistant Examiner — Brigid K Byrd
(74) Attorney, Agent, or Firm — Muncy, Geissler, Olds & Lowe, P.C.

(57) ABSTRACT

The present invention provides a filter device, including a filtering part, a constraining part, a stent part, and a connecting part. The filtering part has a first end and a second end opposite to each other. The constraining part is degradable and at least configured to constrain the first end of the filtering part. The stent part has a first end and a second end opposite to each other. The first end of the stent part is connected to the second end of the filtering part, and disposed coaxial with the filtering part. The connecting part is disposed on one or more of the first end of the filtering part and the second end of the stent part, and is configured to connect to an external mechanism, and the constraining part is further configured to constrain the second end of the stent part when the connecting part is disposed at the second end part (Continued)

of the stent part. The present invention can be taken out from the human body and can also be partially degraded in the human body so that the occurrence rate of long-term complications is reduced, and secondary surgery can thus be avoided.

8 Claims, 10 Drawing Sheets

(52) U.S. Cl.
CPC ... *A61F 2002/016* (2013.01); *A61F 2002/018* (2013.01); *A61F 2310/00365* (2013.01)

(58) Field of Classification Search
CPC . A61F 2002/016; A61F 2002/018; A61F 2/04
See application file for complete search history.

(56) References Cited

U.S. PATENT DOCUMENTS

| | | | |
|---|---|---|---|
| 2009/0105747 A1* | 4/2009 | Chanduszko | A61F 2/01 606/200 |
| 2010/0016881 A1* | 1/2010 | Fleck | A61F 2/01 606/200 |
| 2010/0042135 A1* | 2/2010 | Shirley | A61F 2/01 606/200 |
| 2010/0183230 A1 | 7/2010 | Horan et al. | |
| 2010/0185229 A1 | 7/2010 | Horan et al. | |
| 2010/0228281 A1* | 9/2010 | Gilson | A61F 2/0103 606/200 |
| 2011/0152919 A1* | 6/2011 | Chin | A61F 2/0105 606/200 |
| 2012/0277787 A1* | 11/2012 | Eggers | A61F 2/01 606/200 |
| 2013/0158591 A1* | 6/2013 | Koehler | A61F 2/01 606/200 |
| 2013/0253573 A1* | 9/2013 | Agnew | A61F 2/0105 606/200 |
| 2014/0188152 A1* | 7/2014 | Aggerholm | A61F 2/01 606/194 |
| 2016/0038270 A1* | 2/2016 | Horan | A61F 2/01 606/200 |
| 2016/0113753 A1* | 4/2016 | Klausen | A61F 2/0105 606/200 |

FOREIGN PATENT DOCUMENTS

| | | |
|---|---|---|
| CN | 106491239 A | 3/2017 |
| CN | 206342563 U | 7/2017 |
| EP | 1574169 A2 | 2/2000 |
| WO | WO2012/118696 A1 | 9/2012 |

\* cited by examiner

FILTER DEVICE

TECHNICAL FIELD

The present invention relates to the technical field of medical instruments and, more specifically, to a filter device.

BACKGROUND

Venous Thrombo Embolism (VTE) is a clinically common disease with high incidence rate and mortality. VTE includes Deep Vein Thrombosis (DVT) and Pulmonary Embolism (PE). DVT often occurs in the veins of lower extremity, and PE is mainly caused by detachment of the thrombosis which is formed in venous system or right heart into the pulmonary artery, which is the main cause of disease and death.

Anticoagulant therapy is always the golden standard for VTE treatment, with the goal of preventing the forming of thrombosis, preventing PE, and restoring the patency of embolized veins. Moreover, when the patient has to terminate anticoagulation due to anticoagulation contraindications or hemorrhagic complications, implantation of the Vena Cava Filter (VCF) can effectively intercept the detached thrombus and prevent the occurrence of fatal pulmonary embolism. Early VCFs are mainly permanent filters, and the disadvantage of this type of filters is that it is prone to complications such as obstruction of the inferior vena cava in the long term.

In recent years, retrievable VCFs have gradually become the mainstream, and filters can be retrieved from the patients after PE risk is removed, thereby avoiding complications caused by the implantation and long-term stay of filters. However, according to the report, the actual retrieving probability of the retrievable filters in America is about 30%, that is, although most patients have been implanted with a retrievable filter, the filter is not actually retrieved. There are many reasons for this phenomenon. Some patients are reluctant to undergo a secondary surgery, and some patients fail to retrieve the filter successfully.

In order to solve this practical problem, foreign manufacturers have developed filters that do not require secondary surgery, i.e., partially degradable filters. The principle of such kind of filter is that the head end of the filter is defined by a degradable filament to form a filter net. The head end of the filter is unfolded to fit with the vascular wall after the degradable filament is degraded in the blood vessel, and the filter becomes a tubular stent. In such way, it is not required to perform an additional retrieving operation for the filter, and the filter can convert into a stent to reduce the incidence rate of long-term complications caused by the filter.

However, once the partially degradable filter is implanted in the patient, there is no possibility of being retrieved from the human body. Although this type of filters can be converted into a stent, which can reduce the incidence rate of long-term complications caused by the filter, there must be some potential risks since the filter exists in the blood vessel as a metal foreign body for a long time.

SUMMARY OF THE DISCLOSURE

An objective of the present invention is to provide a filter device that can be not only retrieved within a preset time window but also partially degraded in the body beyond the preset time window, thereby reducing the risk of long-term complications after the filter is implanted in the human body.

To achieve the foregoing objective, the present invention provides a filter device, comprising:

a filtering part having a first end and a second end opposite to each other;

a degradable constraining part configured to constrain at least the first end of the filtering part;

a stent part having a first end and a second end opposite to each other, the first end of the stent part being connected to the second end of the filtering part and the stent part being disposed coaxial with the filtering part; and a connecting part disposed at the first end of the filtering part and/or the second end of the stent part and configured to be connected to an external mechanism;

wherein the constraining part is further configured to constrain the second end of the stent part when the connecting part is disposed at the second end of the stent part.

Optionally, the filter device has a head end and a tail end opposite to each other, the first end of the filtering part corresponds to the head end of the filter device, and the second end of the stent part corresponds to the tail end of the filter device.

Optionally, the stent part comprises a support part and a retrieving part when the connecting part is disposed at the second end of the stent part, and the second end of the stent part corresponds to the tail end of the filter device; one end of the support part is connected to the second end of the filtering part, and a further end of the support part or the one end of the support part is connected to one end of the retrieving part; and the one end of the support part serves as the first end of the stent part, a further end of the retrieving part serves as the second end of the stent part, and the further end of the retrieving part is constrained by the constraining part to form the tail end.

Optionally, the support part, in an entire length thereof, is not overlapping with the filtering part in an axial direction of the filter device when the further end of the support part is connected to the one end of the retrieving part.

Optionally, the support part, in a partial or an entire length thereof, is overlapping with the filtering part in an axial direction of the filter device when the one end of the support part is connected to the one end of the retrieving part.

Optionally, the retrieving part comprises a plurality of retrieving rods distributed along a circumferential direction of the support part, and one end of each of the plurality of retrieving rods is connected to the support part, and further ends of the plurality of retrieving rods are constrained together by the constraining part.

Optionally, the further ends of the plurality of retrieving rods are provided with a plurality of connecting holes, and the constraining part comprises a constraining body which passes through the plurality of connecting holes and is fixed.

Optionally, at least one end of the constraining body is fixed, and a further end of the constraining body passes through the plurality of connecting holes and then is connected to the one end of the constraining body.

Optionally, the stent part comprises a support part when the connecting part is disposed at the first end of the filtering part; the support part has one end connected to the second end of the filtering part, and a further end that is expanded.

Optionally, the support part, in a partial or an entire length thereof, is overlapping with the filtering part in an axial direction of the filter device when the first end of the stent part corresponds to the tail end of the filter device.

Optionally, the support part, in an entire length thereof, is not overlapping with the filtering part in an axial direction of the filter device when the second end of the stent part corresponds to the tail end of the filter device.

Optionally, the first end of the filtering part is provided with a plurality of connecting holes, and the constraining part comprises a constraining body which passes through the connecting holes and is fixed.

Optionally, at least one end of the constraining body is fixed, and a further end of the constraining body passes through the plurality of connecting holes and then is connected to the one end of the constraining body.

Optionally, the connecting part has a recessed space configured to engage with an external mechanism.

Optionally, the connecting part is a hook or a tube having a notch.

In view of the above, the filter device provided by the present invention includes a filtering part, a degradable constraining part, a stent part, and a connecting part. The filtering part has a first end and a second end opposite to each other. The constraining part is configured to at least constrain the first end of the filtering part. The stent part has a first end and a second end opposite to each other. The first end of the stent part is connected to the second end of the filtering part, and disposed coaxial with the filtering part. The connecting part is disposed on one or more of the first end of the filtering part and the second end of the stent part, and is configured to connect to an external mechanism, and the constraining part is further configured to constrain the second end of the stent part when the connecting part is disposed at the second end of the stent part. The filter device of such a structure can be taken out from the human body by means of the connecting part in the case that the patient does not require the protection provided by the filter device, and can be converted into a tubular stent by means of the degradable constraining part to establish a blood flow channel in the human body. The two operable modes on one hand can reduce the incidence rate of long-term complications such as vena cava blockage and perforation, and on the other hand avoid the secondary surgery and thus can alleviate the suffering of the patients.

DESCRIPTION OF REFERENCE NUMERALS

10, 20, 30 respectively denote a filter device; 1, 1', 1" respectively denote a filtering part; 101 denotes a connecting hole; 2 denotes a constraining part; 201 denotes a binding filament; 3 denotes a support part; 301 denotes a barb; 4 denotes a connecting part; 5 denotes a retrieving part; 501 denotes a connecting hole; 502 denotes a retrieving rod.

DETAILED DESCRIPTION

To make the objectives, advantages and features of the present invention clearer, the filter device proposed by the present invention will be further described in detail below with reference to FIGS. 1-10. It should be noted that the drawings are in a very simplified form and use non-precise proportions, and are only intended to conveniently and explicitly assist in describing the objectives of embodiments of the present invention.

Embodiment 1

Figure 1:
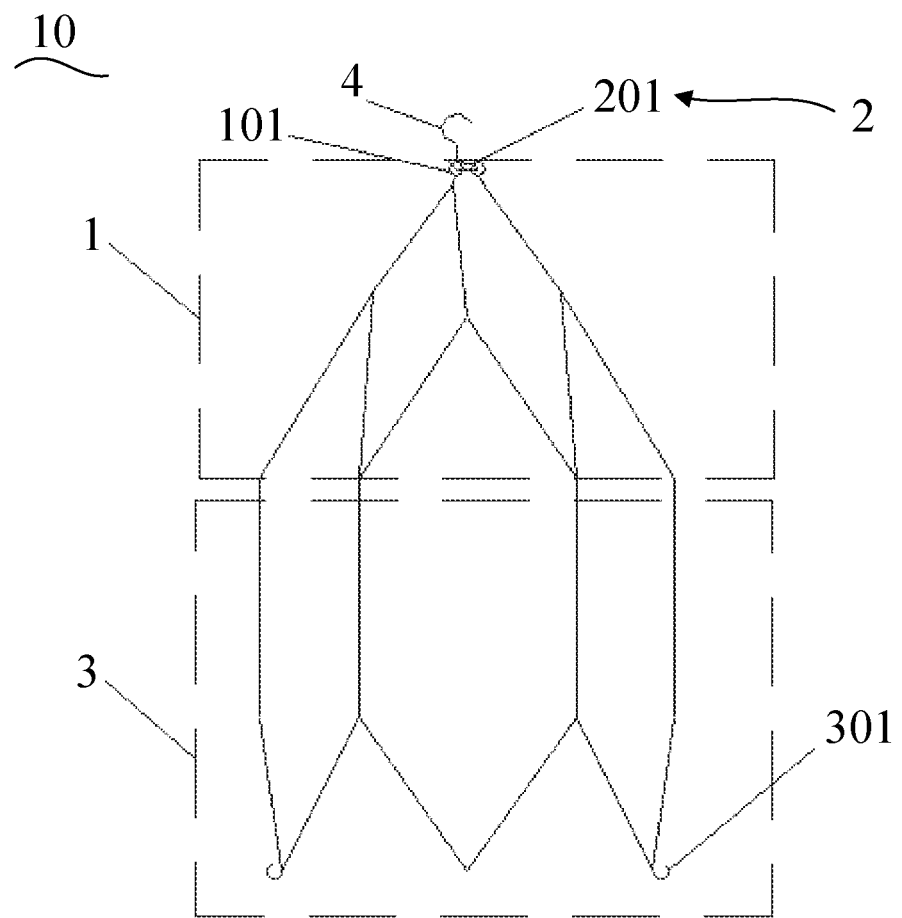
FIG. 1 is a schematic structural diagram of a filter device according to Embodiment 1 of the present invention.

FIG. 1 is a schematic structural diagram of a filter device according to Embodiment 1 of the present invention. As shown in FIG. 1, the filter device 10 includes a filtering part 1, a constraining part 2, a support part 3, and a connecting part 4. The filtering part 1 has a first end and a second end opposite to each other. The filter device 10 has a head end and a tail end opposite to each other. The first end corresponds to the head end and is generally one end adjacent to the heart, i.e., a proximal end. The support part 3 is used as a stent part in this embodiment and has a first end and a second end opposite to each other.

The constraining part 2 is made of a biodegradable material that is constrained to the first end of the filtering part 1 to close the first end of the filtering part 1 so as to trap the thrombus. The second end of the filtering part 1 is connected to the first end of the support part 3. The filtering part 1 is formed as a filter net structure under the constraint of the constraining part 2, and the filter net structure may be conical and has the functions of filtering thrombus and preventing pulmonary embolism and the like. Moreover, after implanted into the human body for a period of time, the first end of the filtering part 1 is unbound and open after the constraining part 2 is completely degraded, and accordingly the function of filtering the thrombus is no longer provided.

The support part 3 is tubular and disposed coaxial with the filtering part 1. The first end of the support part 3 is connected to the filtering part 1, and the second end of the support part 3 is open. In this embodiment, the second end of the support part 3 corresponds to the tail end of the filter device 10, and the tail end is generally one end away from the heart, i.e., a distal end. Moreover, the entire length of the support part 3 does not overlap with the filtering part 1 in the axial direction of the filter device 10. For example, the filtering part 1 is located at one side of the support part 3 and does not overlap with the support part 3. The first end of the support part 3 has a first edge, the second end of the support part 3 has a second edge, and the contours of the first edge and the second edge are not limited to a zigzag shape, a wave shape, or the like.

The support part 3 can structurally support the filtering part 1, and can be centrally disposed in the blood vessel before the filtering part 1 loses the constraint from the constraining part 2, and can be fitted well with the vascular wall without causing displacement. Centering herein means that the filtering part 1 is located in the middle of the blood vessel, and its vertex (first end) is substantially on the central axis of the blood vessel.

In order to retrieve the filter device 10, the first end of the filtering part 1 is provided with the connecting part 4. One end of the connecting part 4 is connected to the filtering part 1, and the other end of the connecting 4 is configured to connect an external mechanism. The filter device 10 can be pulled by the connecting part 4 when the connecting part 4 is connected to the external mechanism, and before the filtering part 1 loses the constraint from the constraining part 2, so that the filter device 10 enters a predetermined channel (e.g. a sheath) and then is taken out from the human body.

In this embodiment, the filter device 10 can be selected to be taken out within a preset time window, and the preset time window is shorter than the time required for completely degrading the constraining part 2. More preferably, the preset time window is set to begin at the moment that the filter device 10 is implanted into the human body and end before the filter device 10 is fused to be integrated with the vascular wall. Specifically, the retrieving period, which begins at the moment that the filter device 10 is implanted into the human body and ends at the moment that the filter device 10 is fused to be integrated with the vascular wall, can be determined through tests, and the preset time window may be selected to be shorter than the retrieving period.

If the filter device 10 is not taken out beyond the preset time window, or the filter device 10 is not taken out for other reasons, the filter device 10 is converted into a tubular stent as a whole after the constraining part 2 is completely degraded. In this case, the first end of the filtering part 1 is open, and the second end of the support part 3 is also in an open state. Further, the tubular filter device 10 can be fitted with the vascular wall to form a blood flow channel, thereby ensuring normal circulation of blood.

If the connecting part 4 is provided at the proximal end of the filter device 10, the filter device 10 can only be retrieved through a jugular vein pathway. In this case, the first end of the filtering part 1 is close to the heart after being implanted into the human body. During retrieval, an external mechanism and the sheath are introduced through the jugular vein, and the filter device 10 is pulled into the sheath by connecting the external mechanism to the connecting part 4. The external mechanism can be a conventional surgical catcher.

The filter device 10 of this embodiment is particularly suitable for patients requiring temporary protection from filter. There are two operation modes after the filter device 10 is implanted into the patient's body.

The first operation mode is to completely take out the filter device 10 from the patient's body through an interventional surgery within a preset time window.

The second operation mode is to partially degrade the filter device 10 in the patient's body beyond the preset time window (that is, the constraining part 2 is degraded) so that the filter device 10 no longer has a filtering function and is converted into a tubular stent.

Compared with the permanent filter, the filter device 10 provided by this embodiment can be taken out from the human body or converted into a tubular stent in the case that the patient does not require the protection from the filter device. Such two alternative modes can reduce the incidence rate of long-term complications such as vena cava blockage and perforation.

Compared with the retrievable filter, the filter device 10 provided by the present invention makes it possible to avoid the secondary surgery, and the filter device 10 is able to be converted into a tubular stent even if the filter device 10 cannot be taken out beyond the preset time window or due to other reasons, thereby reducing the incidence rate of various complications caused by long-term stay of the filter device 10.

Further, the time for the complete degradation of the constraining part 2 depends on many factors, including the molecular weight, crystallinity and hydrophilicity of the materials used, the volume of each component, the surface area, and environmental factors, etc., and the specific time for the complete degradation can be selected by those skilled in the art as needed. However, those skilled in the art should know that the time for the complete degradation of the constraining part 2 is the time when the constraining part 2 is implanted into the human body until the (main) physical property is completely lost. In this case, the constraining part 2 does not constrain the filtering part 1 at all.

In this embodiment, the constraining part 2 is specifically a degradable binding filament 201. The binding filament 201 is completely degraded within a predetermined period of time, so as to disconnect from the filtering part 1, thereby releasing the binding at the first end of the filtering part 1. However, the present invention includes, but is not limited to, a filament, and may also be a cord, wire, or the like.

Preferably, at least one end of the binding filament 201 is fixedly disposed on the first end of the filtering part 1 to ensure that at least one end of the binding filament 201 can still be connected to the first end of the filtering part 1 after broken, thereby ensuring that the degradation residue of the binding filament 201 does not fall into the blood to cause an adverse event such as embolism. The residue is fitted with the vascular wall after the binding filament 201 is broken, and wrapped through the endothelialization formed gradually and then degraded in the tissue. Optionally, the material of the binding filament 201 is selected from a degradable metal material such as a magnesium alloy, a pure iron, or a zinc alloy, or a degradable polymer material such as polylactic acid.

As shown in FIG. 1, the first end of the filtering part 1 can be provided with a plurality of connecting holes 101, and the other end of the binding filament 201 passes through the connecting holes 101 and constrains the first end of the filtering part 1 in a knotted manner, to constrain the connecting holes 101 of the filtering part 1 together so that the filtering part 1 is of a filter net structure. The filtering part 1 can be specifically formed by combining a plurality of structural bodies into a mesh structure. The structural body of the filtering part 1 can be a wire, a rod or a tube, and can be processed by laser cutting, weaving or the like. The connecting holes 101 are provided on a part or all of the structural bodies of the filtering part 1.

In an exemplary operation, the support part 3 is provided with barbs 301. The extension direction of the barbs 301 is consistent with the retrieving direction of the filter device 10. The barbs 301 are configured to penetrate the vascular tissue to fix the filter device 10. Certainly, the barbs 301 can also be separated from the vascular tissue in the retrieving process. In this embodiment, each of the barbs 301 is disposed on an edge of the support part 3 away from the filtering part 1, and preferably disposed on a node of the edge. The node is a position where a plurality of structural bodies intersect.

Figure 2A:
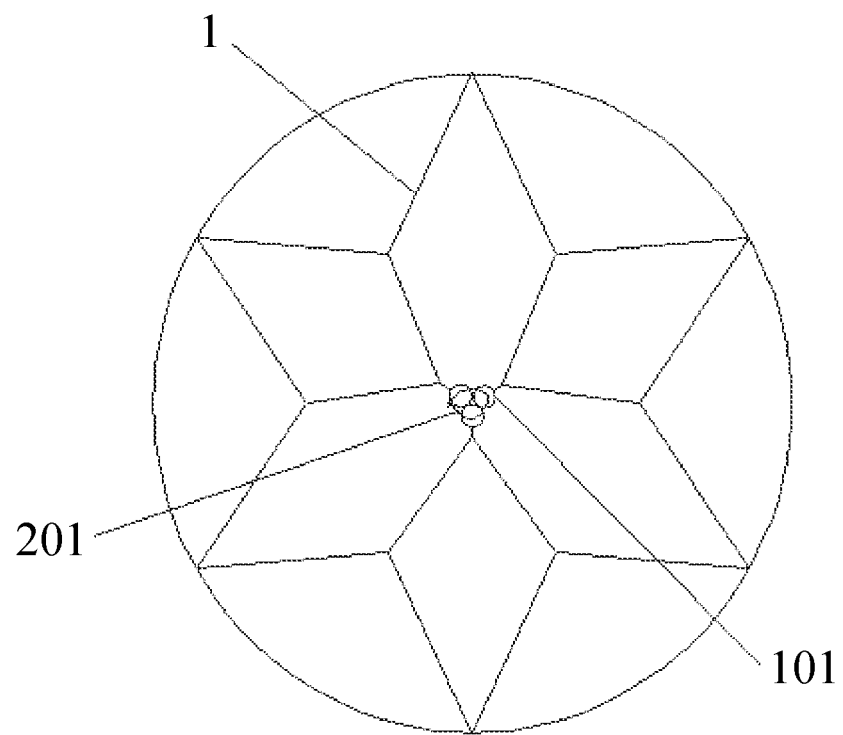
FIG. 2a is a schematic structural diagram of a filter device according to Embodiment 1 of the present invention under a projection from a head end to a tail end.
Figure 2B:
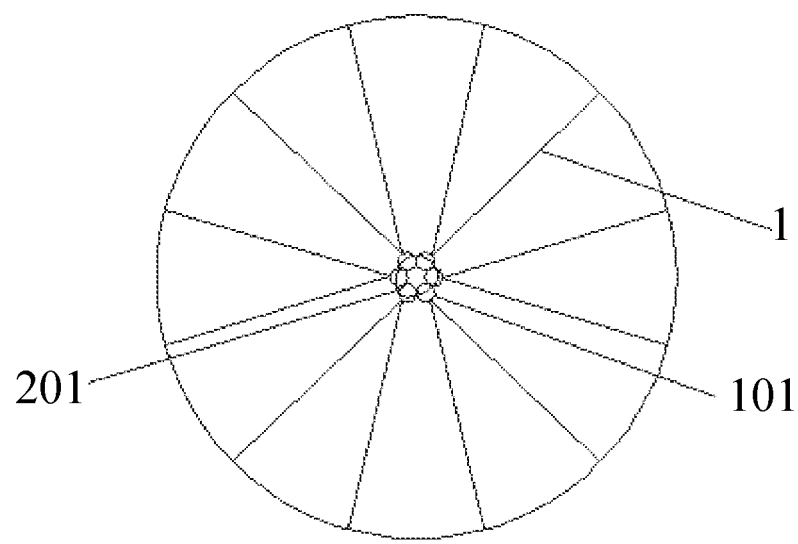
FIG. 2b is a schematic structural diagram of a filter device according to Embodiment 1 of the present invention under a projection from the head end to the tail end.

Further, the filtering part 1 is composed of a plurality of grid units in the same circumferential direction. Each grid unit is composed of a plurality of structural bodies connected end to end. The structural body of the filtering part 1 can also be a wire, a tube or a rod. As shown in FIG. 2a, it is a schematic structural diagram of a filter device according to Embodiment 1 of the present invention under a projection from a head end to a tail end. The filtering part 1 is composed of a plurality of diamond-shaped units in the same circumferential direction, and the number of the diamond-shaped units is preferably 6-8. Alternatively, as shown in FIG. 2b, it is a schematic structural diagram of a filter device according to Embodiment 1 of the present invention under a projection from the head end to the tail end. The filtering part 1 is composed of a plurality of fan-shaped units in the same circumferential direction, and the number of the fan-shaped units is preferably 12-16. Compared with the fan-shaped units, the diamond-shaped units filter the thrombus more evenly, and the thrombus filtering effect is better.

Figure 3A:
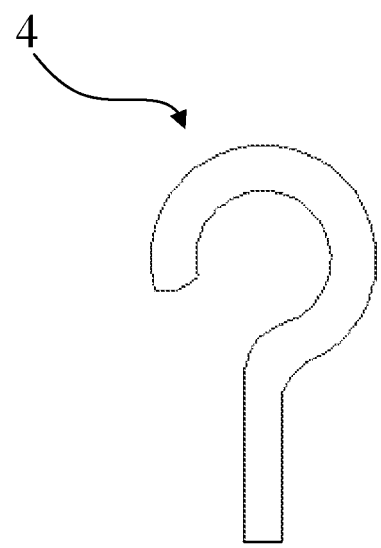
FIG. 3a is a schematic structural diagram of a connecting part according to Embodiment 1 of the present invention.
Figure 3B:
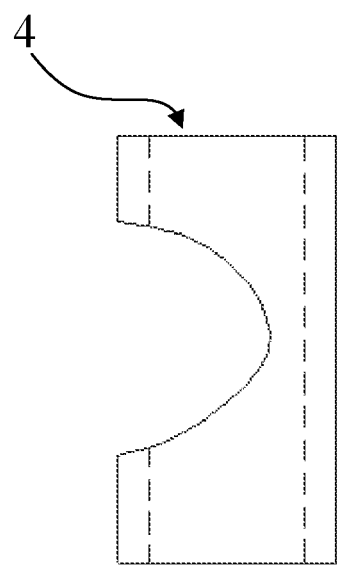
FIG. 3b is a schematic structural diagram of another connecting part according to Embodiment 1 of the present invention.

In this embodiment, the connecting part 4 has a recessed space configured to engage with the external mechanism. As shown in FIG. 3a, the connecting part 4 can be a hook. Alternatively, as shown in FIG. 3b, the connecting part 4 can also be a tube having a notch. In addition, the connecting part 4 and the filtering part 1 can be connected in the following manners.

Figure 4A:
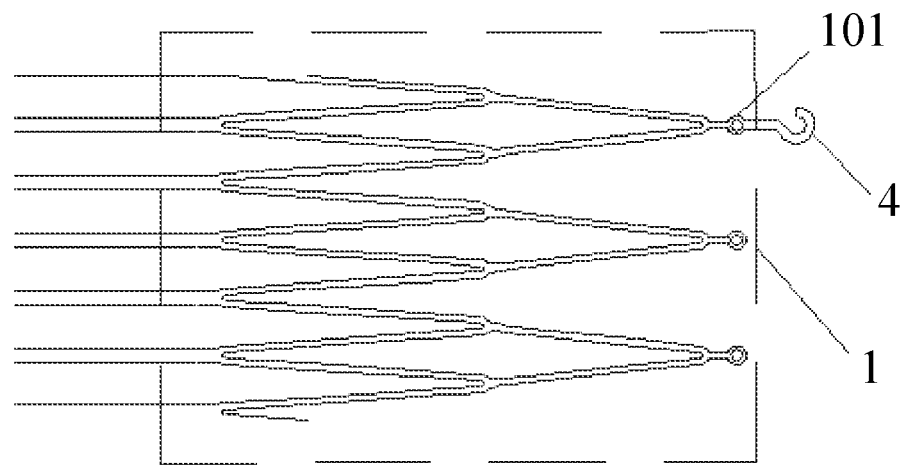
FIG. 4a is a schematic structural diagram showing that the connecting part and a support part are integrated according to Embodiment 1 of the present invention.
Figure 4B:
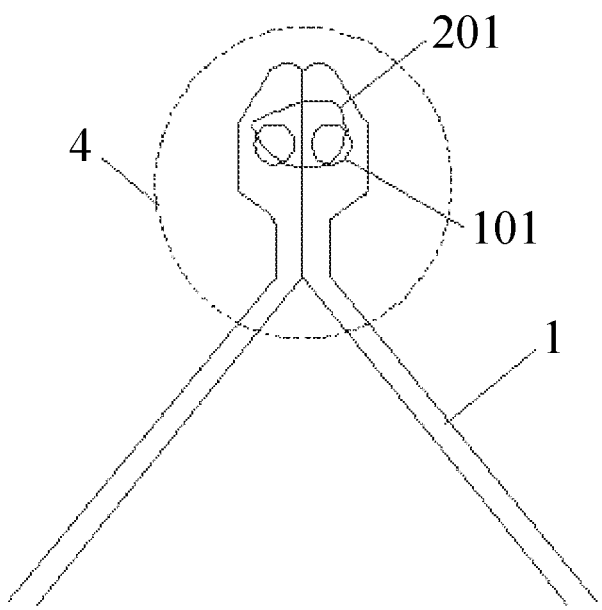
FIG. 4b is a schematic structural diagram of a connecting part formed by a filtering part itself according to Embodiment 1 of the present invention.

1. As shown in FIG. 4a, the structural body of the filtering part 1 in which the connecting holes 101 are formed is cut to directly form the connecting part 4, thereby integrally forming the connecting hole 101 and the connecting part 4. Optionally, the first end of the filtering part 1 has an extending section on which the connecting hole 101 and a hook are formed. The shape and size of the connecting hole 101 are not limited, and a circular hole is preferred since it is convenient to process.
2. The connecting part 4 is welded to a connecting hole 101 on the filtering part 1 to obtain the split connecting part 4 and the filtering part 1. However, the present invention includes but is not limited to welding, and other connecting modes in which the connecting part 4 is connected to the connecting hole 101 are also applicable.
3. As shown in FIG. 4b, a plurality of connecting holes 101 on the filtering part 1 directly form the connecting part 4 in a constrained state. The structure enclosed by the connecting holes 101 is used as the connecting part 4. For example, the catcher can lock the waist portion (i.e., the recessed region) of the connecting part 4 to achieve the engagement.

Figure 5A:
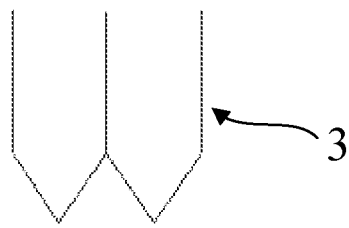
FIG. 5a is a schematic diagram of units constituting a support part according to Embodiment 1 of the present invention.
Figure 5B:
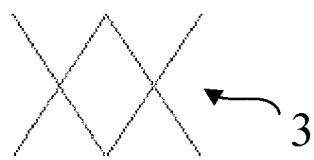
FIG. 5b is a schematic diagram of another kind of units constituting a support part according to Embodiment 1 of the present invention.
Figure 5C:
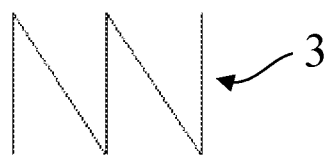
FIG. 5c is a schematic diagram of a further kind of units constituting a support parts according to Embodiment 1 of the present invention.

Further, the first end of the support part 3 is connected to the filtering part 1 through preferably hot melting, and accordingly the fixing effect is better. With continued reference to FIG. 5a in view of FIG. 1, the structural bodies of the support part 3 may be connected end to end to form a plurality of support units. The support units each can be hexagonal, diamond-shaped, etc., and can be fabricated by laser cutting. As shown in FIG. 5b in view of FIG. 1, every two of the structural bodies of the support part 3 are intersected to form a plurality of support units. The shape of the support units is not limited, and the support units can be fabricated by weaving. As shown in FIG. 5c in view of FIG. 1, the structural bodies of the support part 3 are arranged in groups of three and arranged in a Z-shape to form a plurality of support units.

Figure 8:
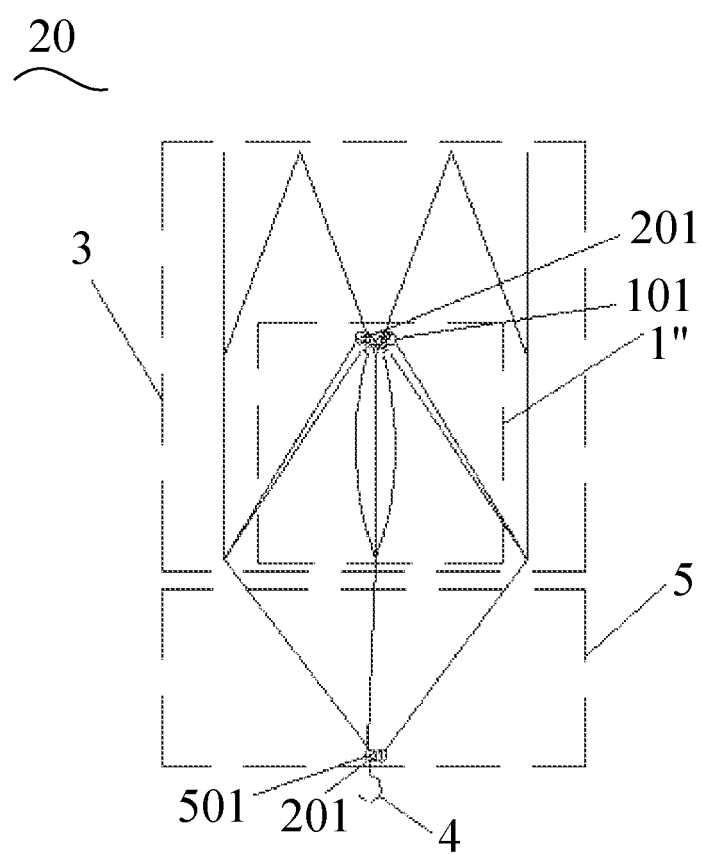
FIG. 8 is a preferred schematic structural diagram of a filter device according to Embodiment 2 of the present invention.

In addition, a part or all of the length of the support part 3 provided in this embodiment may also overlap with the filtering part 1" in the axial direction of the filter device 20 (this solution is not shown, and adaptive reference is made to FIG. 8). In this case, the first end of the support part 3 is connected to the second end of the filtering part 1". Moreover, the first end of the support part 3 corresponds to the tail end of the filter device 20, that is, the second end of the support part 3 is folded at its first end and directed toward the first end of the filter part 1".

Embodiment 2

The filter device 20 provided in this embodiment is basically the same as that in Embodiment 1, and the following description is provided only for describing the differences.

Figure 6:
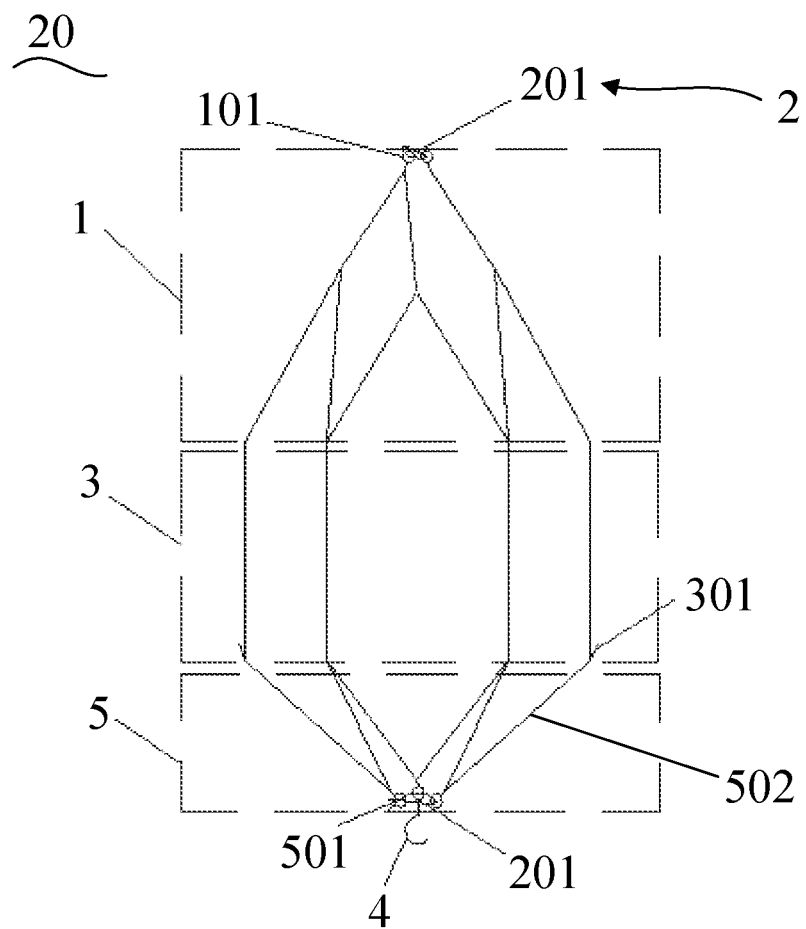
FIG. 6 is a schematic structural diagram of a filter device according to Embodiment 2 of the present invention.

FIG. 6 is a schematic structural diagram of a filter device according to Embodiment 2 of the present invention. As shown in FIG. 6, the filter device 20 includes a filtering part 1, a constraining part 2, a support part 3, and a connecting part 4, and further includes a retrieving part 5. The support part 3 and the retrieving part 5 together constitute the stent part of the present invention. The stent part has a first end and a second end opposite to each other, and the second end of the stent part corresponds to the tail end of the filter device 20.

In this embodiment, the entire length of the support part 3 does not overlap with the filtering part 1 in the axial direction of the filter device 20. Specifically, the first end of the support part 3 is connected to the second end of the filtering part 1, and the second end of the support part 3 is connected to one end of the retrieving part 5. Moreover, the first end of the support part 3 serves as the first end of the stent part, and the other end of the retrieving part 5 serves as the second end of the stent part. The said other end of the retrieving part 5 is constrained by the constraining part 2 to form the tail end. Obviously, the constraining part 2 constrains not only the first end of the filtering part 1 but also the said other end of the retrieving part 5 away from the support part 3 (i.e., the tail end of the filter device 20). The head end and the tail end of the filter device 20 are closed under the constraint of the constraining part 2 to achieve the function of trapping the thrombus.

Specifically, the connecting part 4 is provided only at the tail end of the filter device 20 (i.e., the said other end of the retrieving part 5). One end of the connecting part 4 is connected to the said other end of the retrieving part 5, and the other end of the connecting part 4 is configured to connect an external mechanism. When the connecting part 4 is connected to the external mechanism, the filter device 20 can be retrieved through the connecting part 4 and the retrieving part 5 before the filtering part 1 and the retrieving part 5 lose the constraint from the constraining part 2. Specifically, the external mechanism pulls the filter device 20 through the connecting part 4, and gathers the support part 3 through the retrieving part 5, thereby integrally contracting the filter device 20 so that the filter device 20 can smoothly enter the sheath and thus can be taken out from the human body.

A degradable binding filament 201 may pass through a plurality of connecting holes 101 on the first end of the filtering part 1 for constraint purpose, which is identical to Embodiment 1. Similarly, another degradable binding filament 201 may pass through a plurality of connecting holes 501 on the said other end of the retrieving part 5 for constraint purpose.

Figure 7:
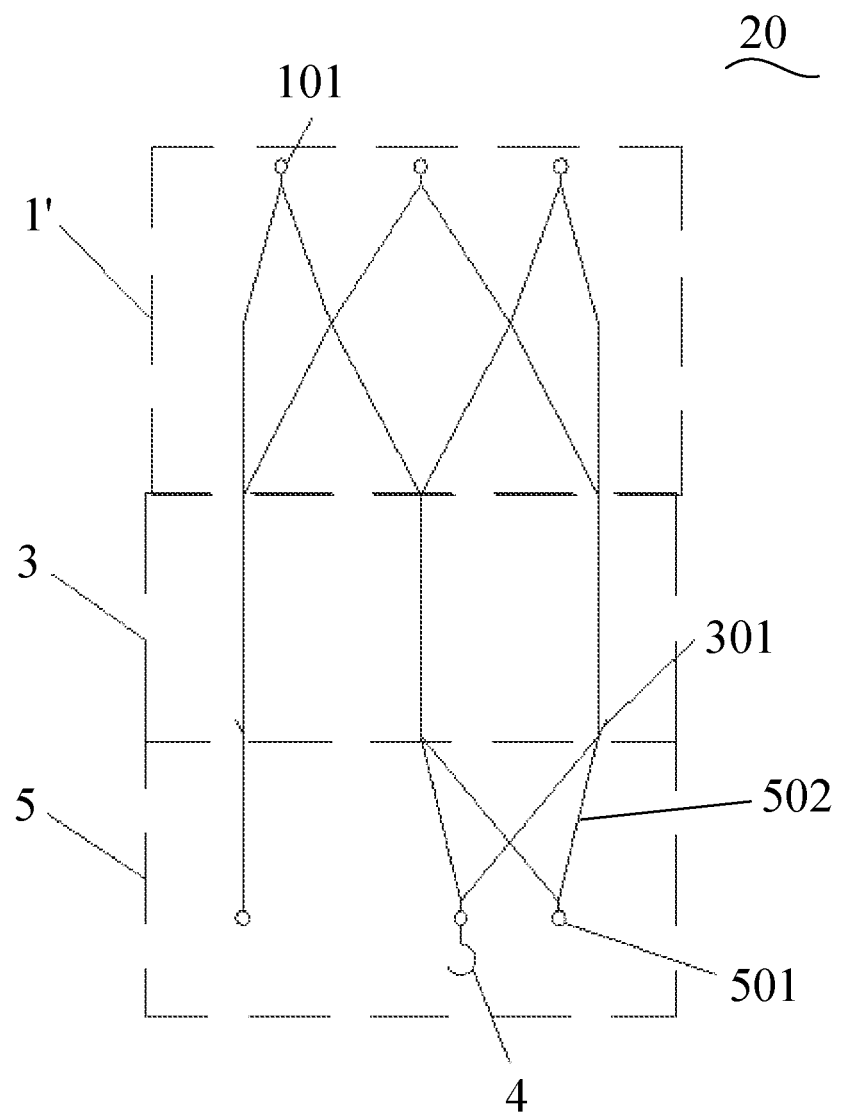
FIG. 7 is a schematic structural diagram of the filter device shown in FIG. 6 after partial degradation.

The constraint at the head end and the tail end of the filter device 20 can be removed when the binding filament 201 is completely degraded and thus broken within a predetermined period of time. FIG. 7 shows a structure in which the filter device 20 shown in FIG. 6 is partially degraded in the blood. As shown in FIG. 7, the filtering part 1 can be converted into the filtering part 1' when the binding filament 201 constrained at the head end is degraded and thus broken in the blood, in such way, the filtering part 1 can be converted from a conical shape to a tubular shape and thus does not have a filtering function any more. The retrieving part 5 can be converted from an inverted cone shape to a tubular shape when another binding filament 201 constrained at the tail end is degraded and thus broken in the blood. In this case, the retrieving part 5 no longer affects the hemodynamics in the vena cava. The filter device 20 of this embodiment is converted into a tubular stent by partial degradation, reducing the effects on hemodynamics to the utmost extent, thereby reducing complications caused by long-term stay of the filter device 20.

If the connecting part 4 is disposed at the distal end of the filter device 20, the filter device 20 can be retrieved through a femoral vein pathway. In this case, after being implanted in the human body, the head end of the filter device 20 is close to the heart, and the tail end is away from the heart. During retrieving, the filter device 20 is smoothly pulled into the sheath by introducing the external mechanism and the sheath through the femoral vein, with the aid of the connection between the external mechanism and the connecting part 4, and the contraction force from the retrieving part 5 against the support part 3. Compared with the retrieving through the jugular vein pathway, the risk of surgery through the femoral vein is low, and the operation is safer and more reliable.

In this embodiment, the retrieving part 5 includes at least a retrieving rod 502, preferably a plurality of retrieving rod 502. The plurality of retrieving rods 502 are distributed along the circumference of the support part 3, and one end of each of the plurality of retrieving rods 502 is connected to the edge of the second end of the support part 3, and the other ends of the retrieving rods 502 are bound together by the binding filament 201. Preferably, the retrieving part 5 has an inverted cone structure under the constraint of the constraining part 2. Each retrieving rod 502 can be connected to the edge of the second end of the support part 3 at any position, and the edge of the first end of the support part 3 is connected to the filtering part 1. Optionally, two retrieving rods together form a connecting hole 501 which can be connected to the connecting part 4.

In the foregoing embodiment, the solution that the support part 3 does not overlap with the filtering part 1 in the axial direction is described. In another embodiment, as shown in FIGS. 8 and 9, a part or all of the length of the support part 3 overlaps with the filtering part 1" in the axial direction of the filter device 20.

The first end of the support part 3 is connected to both the second end of the filtering part 1" and the said one end of the retrieving part 5 when a part or all of the length of the support part 3 overlaps with the filtering part 1" in the axial direction of the filter device 20. Optionally, the first end of the filtering part 1" is located at ½ of the height of the support part 3, and the second end of the filtering part 1" is not lower than the height of the edge (i.e., the lower edge from the perspective of FIG. 8) of the first end of the support part 3. It should be noted that the height of the support part 3 refers to a maximum linear distance between the edge (i.e., the junction with the retrieving part 5) of the first end of the support part 3 fixed to the filtering part 1" and the edge (i.e., the upper edge from the perspective of FIG. 8, i.e., one end close to the heart) of the second end of the support part 3 in the axial direction of the filter device 20. Accordingly, the second end of the filtering part 1" refers to the end away from the heart after being fixed to the support part 3. Preferably, the support part 3 overlaps with the filtering part 1" in the axial direction, which can increase the support strength of the filtering part 1", and the structure is better.

When the support part 3 overlaps with the filtering part 1" in the axial direction, the second end of the filtering part 1" is connected to the edge of the first end of the support part 3, and meanwhile, the retrieving part 5 is also connected to the edge of the first end of the support part 3. Preferably, the first end of the filtering part 1" is also connected to the support part 3. Obviously, in this case, the edge of the second end of the support part 3 is close to the heart.

Figure 9:
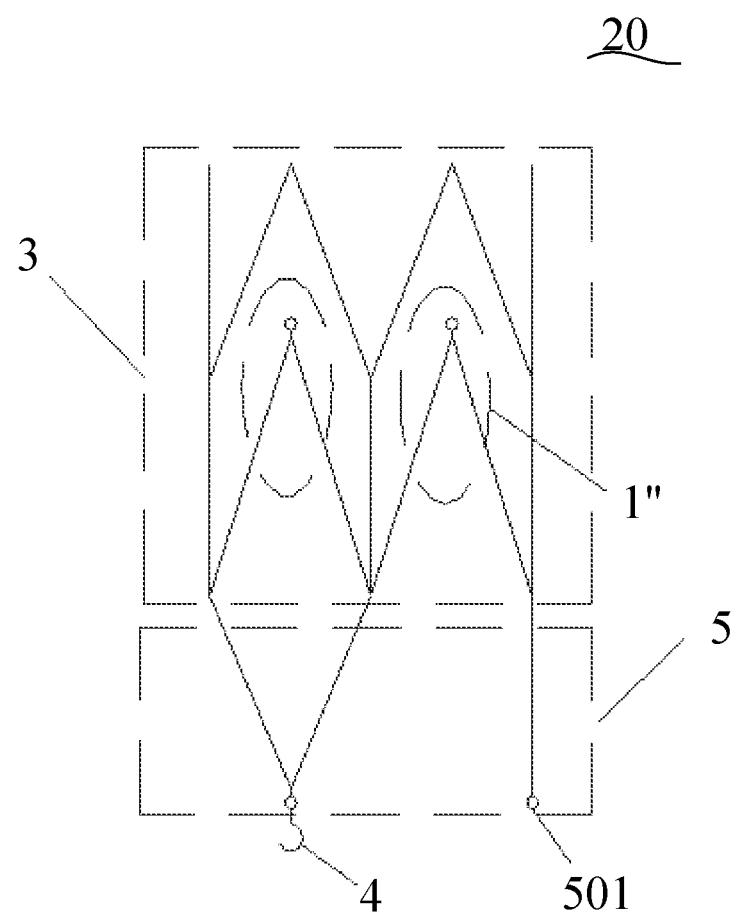
FIG. 9 is a schematic structural diagram of the filter device shown in FIG. 8 after partial degradation.

FIG. 9 is a schematic structural diagram of the partially degraded filter device 20 of FIG. 8. As shown in FIG. 9, after the binding filaments 201 at both ends are degraded, the structural bodies of the filtering part 1" rebound and fits with the vascular wall to be converted into a tubular stent structure and thus does not have a filtering function any more.

Embodiment 3

The filter device provided in this embodiment is basically the same as that in Embodiment 2, and the following description is provided only for describing differences.

Figure 10:
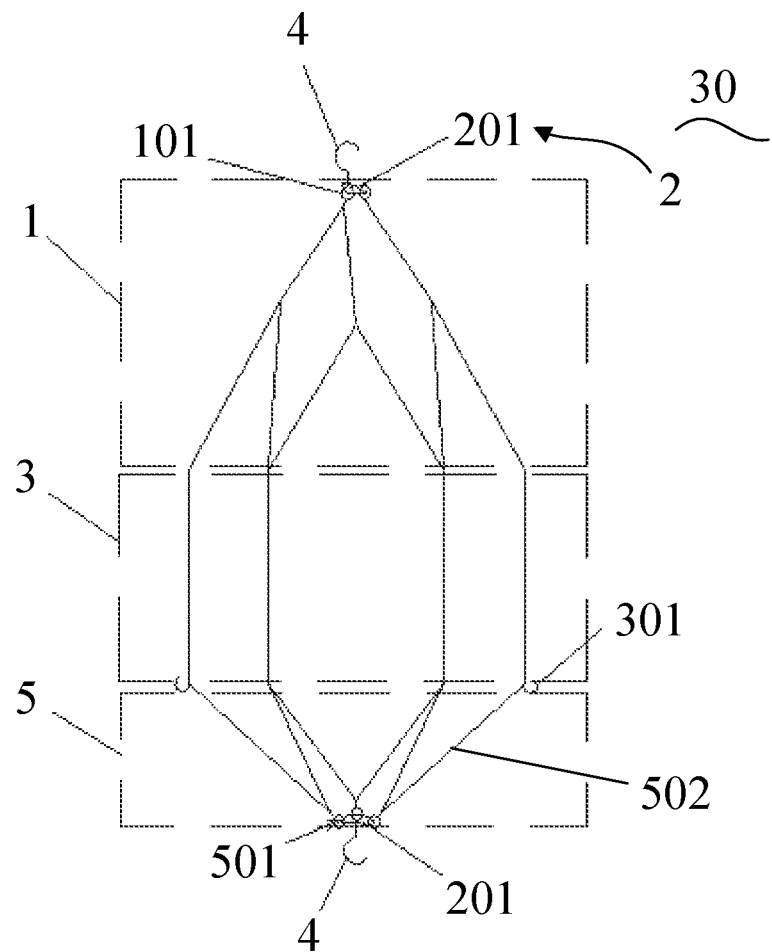
FIG. 10 is a schematic structural diagram of a filter device according to Embodiment 3 of the present invention.

FIG. 10 is a schematic structural diagram of a filter device according to Embodiment 3 of the present invention. As shown in FIG. 10, the filter device 30 includes a filtering part 1, a constraining part 2, a support part 3, a connecting part 4, and a retrieving part 5.

Two connecting parts 4 are provided, one is disposed at the head end of the filter device 30, and the other is disposed at the tail end of the filter device 30. In this case, the filter device 30 can be retrieved through the connecting part 4 located at the head end of the filter device 30, and the filter device 20 can also be retrieved through another connecting part 4 located at the tail end of the filter device 30. Here, for the connection between the connecting part 4 and the head/tail end of the filter device 30 in this embodiment, reference can be made to Embodiments 1 and 2. Details are not described herein again. Obviously, in the specific operation, the filter device 30 can be retrieved through the jugular vein pathway, and can also be retrieved through the femoral vein pathway.

It should be noted that the support part 3 provided in Embodiment 3 can also be folded upwards. The second end of the stent part, i.e., the said other end of the retrieving part always forms the tail end of the filter device when the support part 3 is folded upward.

The foregoing embodiments describe in detail how the constraining part constrains the filtering part and the retrieving part. Certainly, the present invention includes, but is not limited to, the constraining modes listed in the foregoing embodiments, and any transformations made based on the constraining modes provided by the foregoing embodiments fall within the protection scope of the present invention. Those skilled in the art can draw inferences about other cases from one instance according to the contents of the foregoing embodiments.

Finally, compared with the permanent filter, the filter device provided by the present invention can be taken out from the human body or can be converted into a tubular stent in the case that the patient does not require the protection from the filter device, so as to reduce the incidence rate of long-term complications such as vena cava blockage and perforation. Compared with the retrievable filter, the filter device provided by the present invention makes it possible to avoid the secondary surgery, and the filter device is able to be converted into a tubular stent even if the filter device cannot be taken out beyond the preset time window or due to other reasons, thereby reducing the incidence rate of various complications caused by long-term stay of the filter device.

The above description is only a description of the preferred embodiments of the present invention, and is not intended to limit the scope of the present invention. Any changes and modifications made by those skilled in the art according to the above disclosure are all within the scope of protection of the claims.

What is claimed is:

1. A filter device, comprising:
   a filtering part having a first end and a second end opposite to each other along an axial direction of the filtering part;
   a stent part having a first end and a second end opposite to each other along the axial direction, and the stent part being disposed coaxial with the filtering part;
   a degradable constraining part configured to constrain the first end of the filtering part and/or the second end of the stent part; and
   a connecting part configured to be connected to an external mechanism; when the connecting part is connected to the external mechanism, and before the filtering part loses constraint from the constraining part, the filter device is able to be pulled through the connecting part, so that the filter device is taken out from human body;
   wherein the connecting part is disposed only at the second end of the stent part;
   wherein the filter device has a head end and a tail end opposite to each other, the first end of the filtering part corresponds to the head end of the filter device, and the second end of the stent part corresponds to the tail end of the filter device;
   wherein the stent part comprises a support part and a retrieving part; one end of the support part is connected to the second end of the filtering part and to one end of the retrieving part; a further end of the support part serves as the first end of the stent part, a further end of the retrieving part serves as the second end of the stent part, and the further end of the retrieving part is constrained by the constraining part to form the tail end;
   wherein the support part, in a partial or an entire length thereof, is overlapping with the filtering part in an axial direction of the filter device; the first end of the filtering part is connected to the support part at a position thereof other than a position where the second end of the filtering part is connected to the one end of the support part;
   wherein the first end of the filtering part is located at ½ height of the support part along the axial direction of the filtering part.

2. The filter device according to claim 1, wherein the retrieving part comprises a plurality of retrieving rods distributed along a circumferential direction of the support part, and one end of each of the plurality of retrieving rods is connected to the support part, and further ends of the plurality of retrieving rods are constrained together by the constraining part.

3. The filter device according to claim 2, wherein the further ends of the plurality of retrieving rods are provided with a plurality of connecting holes, and the constraining part comprises a constraining body which passes through the plurality of connecting holes and is fixed.

4. The filter device according to claim 3, wherein at least one end of the constraining body is fixed, and a further end of the constraining body passes through the plurality of connecting holes and then is connected to the at least one end of the constraining body.

5. The filter device according to claim 1, wherein the connecting part is a hook or a tube having a notch.

6. The filter device according to claim 1, wherein the connecting part has a recessed space configured to engage with the external mechanism.

7. The filter device according to claim 6, wherein the connecting part is a hook or a tube having a notch.

8. The filter device according to claim 1, wherein the filtering part is composed of a plurality of diamond-shaped units that are located on a same circumferential of the filtering part.

* * * * *